United States Patent [19]

Connolly et al.

[11] Patent Number: 5,179,082
[45] Date of Patent: Jan. 12, 1993

[54] METHOD FOR BLOCKING PLATELET ADHESION TO COLLAGEN

[75] Inventors: Thomas M. Connolly, Harleysville; Jerzy Karczewski, Blue Bell, both of Pa.

[73] Assignee: Merck & Co., Inc., Rahway, N.J.

[21] Appl. No.: 662,225

[22] Filed: Feb. 27, 1991

Related U.S. Application Data

[63] Continuation-in-part of Ser. No. 612,941, Nov. 13, 1990, abandoned.

[51] Int. Cl.$^5$ .............................................. A61K 37/02
[52] U.S. Cl. ..................................................... 514/12
[58] Field of Search ......................................... 514/12

[56] References Cited

U.S. PATENT DOCUMENTS

| | | |
|---|---|---|
| 4,229,540 | 10/1980 | Coan . |
| 4,520,018 | 5/1985 | Simonidesz et al. . |
| 4,578,079 | 3/1986 | Ruoslahti et al. . |
| 4,589,881 | 5/1986 | Pierschbacher et al. . |
| 4,857,508 | 8/1989 | Adams et al. . |
| 4,879,237 | 11/1989 | Ruoslahti et al. . |

OTHER PUBLICATIONS

Gan et al. (1988) J. Biol. Chem. 263 pp. 19827–19832 Echistatin.
Garsky et al. (1989) Proc. Natl. Acad. Sci. USA, 86 pp. 4022–4026. Chemical synethesis of echistatin.
Gan et al. (1989) Gene 79, 159–166.
Dennis et al., Proc. Natl. Acad. Sci., USA, vol. 87, pp. 2471–2475.
Hughes, Chem. Ab., vol. 71 (1969) 20365s.

*Primary Examiner*—Jeffrey E. Russel
*Assistant Examiner*—Choon P. Koh
*Attorney, Agent, or Firm*—Richard S. Parr; Charles M. Caruso

[57] ABSTRACT

A method for blocking platelet adhesion to collagen by contacting platelets with a polypeptide having one of the following sequences:

| | |
|---|---|
| $NH_2$ (Ch) Ala Arg Gly Asp (Cx) COOH | (i) |
| $NH_2$ (Ch) Ala Ala Gly Asp (Cx) COOH | (ii) |
| $NH_2$ (Ch) Ala Arg Tyr Asp (CX) COOH | (iii) |
| $NH_2$ (Ch) Ala Arg Gly Asp (Cy) Z | (iv) | wherein Ch, Cx, Cy are defined amino acid sequences or conservatively substituted amino acid sequences, and Z is $NH_2$ or COOH.

3 Claims, No Drawings

METHOD FOR BLOCKING PLATELET ADHESION TO COLLAGEN

CROSS-REFERENCE TO RELATED APPLICATIONS

This application is a continuation-in-part patent application of U.S. Ser. No. 07/612,941, filed Nov. 13, 1990, now abandoned.

BACKGROUND OF THE INVENTION

Collagen found in the subendothelium is thought to be one of the first thrombogenic stimuli presented to blood at the site of a damaged or diseased vessel wall. In vitro collagen promotes both platelet adhesion and aggregation and subsequent activation of platelets.

Echistatin and its ability to inhibit platelet aggregation by binding to the fibrinogen receptor glycoprotein IIb/IIIa is described in Gan et al. (1988) *J. Biol. Chem.* 263, pp. 19827-19832; Garsky et al. (1989) *Proc. Natl. Acad. Sic. USA* 86, pp. 4022-4026; and Gan et al. (1989) *Gene* 79, 159-166.

Simonidesz et al., U.S. Pat. No. 4,520,018, describes 5-substituted-4-oxo PGI1 derivatives which inhibit blood platelet aggregation induced by ADP, arachidic acid, or collagen and improve blood circulation.

Coan, U.S. Pat. No. 4,229,540, describes a hydrolytic enzyme found in human plasma which inhibits platelet aggregation induced by ADP, epinephrine or collagen.

Rouslahti et al., U.S. Pat. No. 4,578,079, describes the primary cell-binding site of fibronectin as a short amino acid sequence, Arg-Gly-Asp-Ser, that is shared by at least one other adhesive protein, collagen.

SUMMARY OF THE INVENTION

The invention is a composition for inhibiting collagen-stimulated platelet activation by blocking platelet adhesion to collagen, comprising a polypeptide having the following sequence:

| | |
|---|---|
| NH$_2$ (Ch) Ala Arg Gly Asp (Cx) COOH | Seq. ID No. 1 |
| NH$_2$ (Ch) Ala Ala Gly Asp (Cx) COOH | Seq. ID No. 2 |
| NH$_2$ (Ch) Ala Arg Tyr Asp (Cx) COOH | Seq. ID No. 3 |
| NH$_2$ (Ch) Ala Arg Gly Asp (Cy) Z | Seq. ID No. 4 | wherein
Ch is

Glu Cys Glu Ser Gly Pro Cys Cys Arg Asn Cys Lys
Phe Leu Lys Glu Gly Thr Ile Cys Lys Arg or conservative amino acid substitutions thereof;
Cx is Asp Met Asp Asp Tyr Cys Asn Gly Lys Thr Cys Asp
Cys Pro Arg Asn Pro His Lys Gly Pro Ala Thr or conservative amino acid substitutions thereof;
Cy is Asp Met Asp Asp Tyr Cys Asn Gly Lys Thr Cys Asp
Cys or conservative amino acid substitutions thereof; and
Z is NH$_2$ or COOH.

This invention also includes a method for inhibiting collagen-stimulated platelet activation using the composition.

The invention also includes a composition for inhibiting collagen-stimulated platelet activation in a mammal, and a method for inhibiting collagen-stimulated platelet activation in a mammal comprising administering the composition to the mammal, the composition comprising a polypeptide having the following sequence:

| | |
|---|---|
| NH$_2$ (Ch) Ala Arg Gly Asp (Cx) COOH | (i) |
| NH$_2$ (Ch) Ala Ala Gly Asp (Cx) COOH | (ii) |
| NH$_2$ (Ch) Ala Arg Tyr Asp (Cx) COOH | (iii) |
| NH$_2$ (Ch) Ala Arg Gly Asp (Cy) Z | (iv) | wherein
Ch is

Glu Cys Glu Ser Gly Pro Cys Cys Arg Asn Cys Lys
Phe Leu Lys Glu Gly Thr Ile Cys Lys Arg or conservative amino acid substitutions thereof;
Cx is Asp Met Asp Asp Tyr Cys Asn Gly Lys Thr Cys Asp
Cys Pro Arg Asn Pro His Lys Gly Pro Ala Thr or conservative amino acid substitutions thereof;
Cy is Asp Met Asp Asp Tyr Cys Asn Gly Lys Thr Cys Asp
Cys or conservative amino acid substitutions thereof; and
Z is NH$_2$ or COOH.

Preferred polypeptides which inhibit platelet adhesion to collagen are those identified as Seq. Id. Nos. I, II, III, IV and V. Sequences I-III include a terminal amino group for amino acid 1 (Glu) and a terminal carboxy group from amino acid 49 (Thr). Sequence IV includes a terminal amino group for amino acid 1 (Glu) and a terminal carboxy group for amino acid 39 (Gys). Sequence V includes a terminal amino group for amino acid 1 (Glu) and a terminal amino group for amino acid 39 (Cys).

Polypeptide Sequences II, III, IV and V are more preferred for selectively inhibiting platelet adhesion to collagen (versus inhibition of platelet adhesion to fibrinogen). Polypeptide Sequence V is most preferred.

DETAILED DESCRIPTION OF THE INVENTION

Polypeptides useful in the present invention are generally prepared according to Merrifield, *J. Am. Chem. Soc.*, 85, 2149 (1964), which describes procedures for solid phase synthesis, and according to Stewart and Young "Solid Phase Peptide Synthesis" 2nd Ed., Pierce Chemical Company, Rockford, Ill., pp. 1-52. Other equivalent synthesis known in the art can also be used, such as synthesis of Houghten, *Proc. Natl. Acad. Sci.*, 82, 5132 (1985). The contents of these articles are hereby incorporated by reference.

Solid-phase synthesis is commenced from the C-terminus of the peptide by coupling a protected amino acid to a suitable resin, as generally set forth in U.S. Pat. No.

4,244,946, issued Jan. 21, 1982 to Rivier et al., the disclosure of which is incorporated herein by reference. Examples of syntheses of this general type are set forth in U.S. Pat. Nos. 4,305,872 and 4,316,891. Discussion of the solid-phase synthesis of a 41-residue polypeptide is set forth in *Science*, 213, 1394–1397 (September 1981) in an article by Vale et al., which refers to a more detailed discussion of the synthesis, which appears in an article by Marke et al. in *J. Am. Chem. Soc.*, 103, 3178 (1981).

In synthesizing the polypeptides, the carboxyl terminal amino acid, having its alpha-amino group suitably protected is coupled to a chloromethylated polystyrene resin or the like. After removal of the alpha-amino protecting group, as by using trifluoroacetic acid in methylene chloride, the next step in the synthesis is ready to proceed. Other standard cleaving reagents and conditions for the removal of specific amino protecting groups may be used, as described in the open literature.

The remaining alpha-amino- and side-chain-protected amino acids are then coupled stepwise in the desired order to obtain an intermediate compound connected to the resin. As an alternative to adding each amino acid separately in the synthesis, some of them may be coupled to one another prior to the addition to the growing solid-phase chain. The selection of the appropriate coupling reagents is within the skill of the art.

Common to chemical synthesis of peptides is the protection of the labile side-chain groups of the various amino acid moieties with suitable protecting groups at that site until the group is ultimately removed after the chain has been completely assembled. Also common is the protection of the alpha-amino group on an amino acid or a fragment while that entity reacts at the carboxyl group, followed by the selective removal of the alpha-amino-protecting group to allow subsequent reaction to take place at the location. Accordingly, it is common that, as a step in the synthesis, an intermediate compound is produced which includes each of the amino acid residues located in the desired sequence in the peptide chain with various of these residues having side-chain protecting groups. These protecting groups are then commonly removed substantially at the same times so as to produce the desired resultant product following purification.

After the desired amino acid sequence has been completed, the intermediate peptide is removed from the resin support by treatment with a reagent, such as liquid HF, which not only cleaves the peptide from the resin, but also cleaves all the remaining side-chain-protecting groups. The polypeptide can then be purified by gel permeation followed by semipreparative HPLC, as described in Rivier et al., Peptides: Structure and Biological Function (1979) pp. 125–128. A purity of at least 93% or higher (based upon all peptides present) is reasonably obtainable and is preferred for clinical testing and/or use. Purity of 98% is practical; however, for certain in vitro applications, lower purity may be acceptable. Accordingly, the polypeptide is considered useful when it is in substantially pure form which, for purposes of this application, means at least about 50 weight percent, based upon all peptides present.

Synthesis

An automatic peptide synthesizer (Applied Biosystems) is used to prepare a polypeptide of the invention. For synthesizing polypeptides I, II, III, IV and V, for example, threonine is attached to a solid cross-linked polystyrene Pam resin using standard solid phase methodology. The Pam resin may be prepared in accordance with the description in Stewart and Young, pp. 11–12. The resin provides excellent peptide-resin link stability during addition of amino acids and protection group removal. The threonine blocking group is then removed from the amino acyl polymer, and alanine is then coupled to the amino acyl polymer. The cycle of deprotection and coupling is repeated with each amino acid that is to be incorporated into the peptide chain. Each amino acid is added stepwise in order to remove the danger of undesirable racemization.

The following blocking groups were useful during synthesis steps involving these individual amino acids.
Histidine—benzyloxymethyl
Aspartic Acid—cyclohexyl esters
Glutamic Acid—cyclohexyl esters
Cysteine—4-methylbenzyl
Serine—benzyl
Arginine—tosyl
Lysine—chlorobenzyloxycarbonyl
Threonine—benzyl
Tyrosine—bromobenzyloxycarbonyl Double coupling is an important technique to be used during addition of amino acids.

Critical steps during synthesis of the polypeptides occur after the last amino acid has been added, at which point the finished solution must be treated to obtain proper molecular conformation, and to completely preserve the sequence.

After the last amino acid is added to the sequence, but just prior to cleavage of the polypeptide from the resin, the N-terminal Boc group is removed.

After removal of the protection groups, the resin-peptide is treated with HF. In order to avoid alkylation of residues in the polypeptide, (for example, alkylation of methionine, cysteine, and tyrosine residues) it is necessary to include scavengers in the HF reaction mixture. In accordance with the invention, the scavenger to be used is a thio-containing scavenger, preferably a thiocresol and cresol mixture. This scavenger will minimize the oxidation of methionine residues to sulfoxides. After treatment with the above-described HF mixture, the resin is washed with ether, and immediately transferred to a large volume of dilute acetic acid to solubilize and minimize intermolecular cross-linking. A 250 mM polypeptide concentration is diluted in about 2 liters of 0.1 M acetic acid solution. This procedure contrasts greatly with the procedure which would normally be followed (e.g. where a similar polypeptide concentration would be dissolved in about 50–100 ml of a dilute acetic acid solution). The solution is then stirred and its pH adjusted to about 8.0 using ammonium hydroxide. Upon pH adjustment, the polypeptide takes its desired conformational arrangement.

By following the described procedure, one can produce polypeptides having high levels of cysteine residues while minimizing intermolecular cross-linking and undesirable conformational arrangement.

EXAMPLE 1

Assembly of the polypeptide identified below (Sequence ID No. 1) was achieved by the Merrifield solid phase method Kent and Clark-Lewis (1985) *Synthetic Peptides in Biology and Medicine Proc.* Labsystems Res. Symp., Eds. Alitalo et al., Elsevier, Netherlands, pp. 29–57; and Merrifield (1963) *J. Amer. Chem. Soc.*, Vol. 85, pp. 2149–2154.

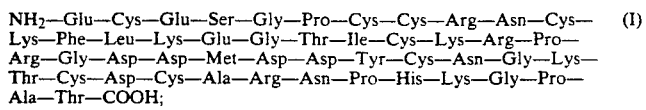

NH₂—Glu—Cys—Glu—Ser—Gly—Pro—Cys—Cys—Arg—Asn—Cys— (I)
Lys—Phe—Leu—Lys—Glu—Gly—Thr—Ile—Cys—Lys—Arg—Pro—
Arg—Gly—Asp—Asp—Met—Asp—Asp—Tyr—Cys—Asn—Gly—Lys—
Thr—Cys—Asp—Cys—Ala—Arg—Asn—Pro—His—Lys—Gly—Pro—
Ala—Thr—COOH;

Appropriate selection of sidechain protection was made in an effort to minimize the formation of by-products during synthesis and HF deprotection. A double coupling protocol was used for peptide-resin assembly and coupling efficiency monitored by ninhydrin analysis of residual free amine Sarin et al. (1981) *Anal. Biochem.* Vol. 117, pp. 147-157. Coupling yields were greater than 98.5% in all but three cycles. The additional couplings of Arg⁹ and Arg²² were performed four times and Ile¹⁹ three times. Following these repeated couplings the ninhydrin analysis was improved to a coupling completion level greater than 97%. The final 49-peptide resin which was isolated in a 93% overall yield, was cleaved from the resin suing the high HF procedure (Tam et al. (1983) *J. Amer. Chem. Soc.*, Vol. 105 pp. 6442-6455) in the presence of p-cresol and p-thiocresol as scavengers. Use of anisole as a scavenger or the application of the low-high HF procedure (Tam et al. ibid.) provided to be less satisfactory due to the generation of complex and difficult to purify mixtures. Following HF treatment the crude reduced product was subjected to air oxidation in ammonium acetate buffer. Probe oxidation at pH 6.5, 7.0, 7.5 and 8.0 over a period of 4 days indicated the optimum pH to be 8.0. Completeness of reaction was established by Ellman analysis and analytical HPLC. The crude product was purified used preparation HPLC by loading the oxidation reaction directly onto a C₁₈-silica reverse-phase column. This technique allowed efficient concentration of 4 liters of solution containing crude polypeptide onto the column support followed by a gradient elution for the isolation of the purified product. After a single pass, the product peak was greater than 95% pure. A second gradient elution of the product produced material which was homogeneous by analytical HPLC in the same solvent system in a 4% overall yield. Application of this concerted purification technique enabled use to isolate the protein with a high level of purity.

The product was characterized for structure and purity. Amino acid analysis after 70 hr acid hydrolysis and performic acid oxidation showed expected values. Sequence analysis carried out for 47 cycles gave the expected results. Within the limits of detection (10%) proton NMR in D₂O established the absence of methionine oxide. The NMR also indicated that alkylation of side-chain functionalites had not occurred. Amino acid composition, following 70 hr acid hydrolysis, of CNBr treated protein was consistant with the expected conversion of methionine to homoserine. This observation further established the absence of methionine sulfoxide.

In preliminary in vivo studies, synthetic polypeptide I was shown to be a very effective antithrombotic agent.

Detailed Procedure

Box-O-benzylthreonine-PAM resin, Boc protected amino acids and all other reagents required for synthesis on the Applied Biosystems 430 A (ABI) peptide synthesizer were obtained from the manufacturer. Sidechain protected Asp, Glu and His were supplied by Bachem, Inc. The solvents dimethylformamide (DMF) and methylene chloride (CH₂Cl₂) were obtained from Burdick and Jackson. Dithiothreitol (DTT) was purchased from Bethesda Res. Labs. Dithioerythritol (DTT) was obtained from Chemical Dynamics. p-cresol and p-thiocresol were obtained from Aldrich Chemical Co.

Polypeptide I Synthesis

Starting with 0.50 mM (0.69 g) of Boc-Thr(Bzl)O-Pam-resin (substitution at 0.72 mM of Thr/g of resin) the synthesis was carried out in a stepwise manner using the ABI automated peptide synthesizer. Kent and Clark-Lewis (1985) *Synthetic Peptides in Biology and Medicine*, Proc. Labsystems Res. Symp., Eds., Alitalo et al., Elsevier, Netherlands pp. 29-57. The amino acids were introduced using the manufacturer's prepacked cartridges (2 mM each). Sidechain protection was Arg (Tos), Asp (OcHx), Cys (Meb), Glu (OcHx), His (Bom) Lys[Z(Cl)], Ser (Bzl), Thr (Bzl), Tyr[Z(Br)]. [Tos, Tosyl; cHx, cyclo-hexyl; Meb. 4-methylbenzyl; Z(Cl), 2-chlorobenzyloxycarbonyl; Bom, benzyloxymethyl; Bzl, benzyl; Z(Br), 2 bromobenzyloxycarbonyl]. Double coupling with symmetric anhydrides (performed in CH₂Cl₂ followed by solvent exchange with DMF) were used for all Boc-protected amino acids except for Arg (Tos), Asn and His (Bom), where hydroxybenzotriazole esters in DMF were used in a double coupling protocol. In order to protect against undesired acid-catalyzed oxidations of Cys and Mt (Draper et al. (1973) *J. Med. Chem.* Vol. 16, pp. 1326-1329) during trifluoroacetic acid (TFA) deblocking, 0.1% (wt/V) DTE was added as a scavenger. Following the coupling of N-terminal Glu the Boc group was removed using TFA and the peptide-resin was dried. The final weight of N-terminal deblocked peptide-resin was 4.15 g.

HF Cleavage and Oxidation

The assembled peptide-resin (2.0 g) was suspended in a mixture of 3 ml of 1:1 (v:v) p-thiocresol/p-cresol in an HF apparatus (Peninusula Labs. Inc., Type 1B). The system was evacuated with a mechanical vacuum pump and HF condensed (30 mL) using liquid nitrogen cooling. After stirring at 0°-5° C. for 1½ hr the reaction mixture was evaporated in vacuo using a liquid nitrogen trap (20-30 min). The residue was triturated with ether, filtered and washed 3 times with additional ether. The filtered residue was immediately transferred to 4 liters of a stirred solution of dilute acetic acid (0.4%/H₂O). After stirring for several minutes the pH of the mixture was adjusted to 8.0 with ammonium hydroxide. Following filtration to remove resin, the crude oxidation product was maintained without stirring at 5° C. (18 hr) and subsequently at ambient temperature (19°-20° C.) for 3 days. Analytical HPLC was used to monitor the progress of the oxidation. A qualitative Ellman test (Habeeb, *Methods in Enzymology* (1972), Eds. Hirs and Timasheff, Academic Press New York pp. 457-464) was used to monitor the disappearance of free sulfhydryl groups before proceeding with purification. This test was performed on a 1 ml sample which was lyophilized in order to remove residual p-thiocresol.

Purification of Oxidized Polypeptide I

The crude oxidized solution (4 l) was acidified by addition of acetic acid (10 ml) and pumped directly onto a $C_{18}$-silica (5×30 cm, 15 m, 300 A) cartridge (Waters Associates). The product was purified using preparation HPLC (Separations Technology, Inc.). A step gradient (100 mL increments) which was generated from 1 liter each of successively increasing concentrations of mobile phase. A flow rate of 70 mL/min was used to elute the product. Homogeneous (>95%) fractions as determined by RP-HPLC (Vydac $C_{18}$, 218TP5415) were pooled and lyophilized to give 72 mg of product. The semi-pure product was contaminated with a less polar component as a shoulder to the product peak. The product was further purified by repassage on HPLC in the same manner as described above to yield echistatin (54 mg). Based on 0.25 mM of starting resin this weight represents a 4 percent overall yield. Homogeneity was demonstrated by analytical HPLC. Coinjection of synthetic product with native material gave a single peak. Product was further characterized by amino acid analysis after hydrolysis with 6N HCl and by automated Edman degradation (ABI 470A Protein Sequencer).

A maximum of 1.9 percent preview was observed. The high yield of PTH amino acids from the first step also demonstrated that cyclization of the C-terminal Glu to pyro-Glu had not occurred.

Reduction and Refolding of Polypeptide I

Polypeptide I (0.50 mg) was dissolved in 1 ml of 0.07 M pH 8.0 ammonium acetate (10 mM DTT) and the course of reduction followed by analytical HPLC. After 1 hr the starting material was converted quantitatively to a single reduced product. Dialysis (24 hr) of the reduced product using a 12 mm diameter, 1000 MW cutoff, celluose tubing (Spectrum Medical Inc.) against (4 l) of a 0.07 M ammonium acetate buffer (pH 8.0) produced only echistatin. In order to demonstrate that the polypeptide was in its fully reduced form prior to reoxidation, the DTT reduction was repeated as described but in the presence of 6M guanidine hydrochloride. Analytical HPLC confirmed that the reduced products had identical retention times. Isolation of reduced polypeptide, by semi-preparative HPLC, followed by quantitative Ellman analysis (Habeed, ibid.) showed the product to be in the octahydro form.

EXAMPLE 2

The polypeptide prepared according to Example 1 is shown to inhibit platelet adhesion to collagen.

Polystyrene 96-well microtiter plates (Costar, Cambridge, MA) are coated with 100 ml per well of 40 mg/ml collagen dissolved in 5 mM acetic acid for 1 hour at room temperature followed by blocking of the non-specific cell binding sites by addition of 200 ml of 10 mg/ml heat-denatured BSA for 1 hour. Control wells are coated with BSA only. The wells are rinsed three times with HEPES buffered saline (HBS) containing 20 mM HEPES, pH 7.4, 0.14 M NaCl, and 2 mM $MgCl_2$. 100 ml of washed platelets are incubated with various concentrations of polypeptide I or buffer as a control for 5 minutes at room temperature and then added to each collagen coated well and incubated at room temperature for 45 minutes. Nonadherent platelets are removed by aspiration, and the wells are rinsed three times with 200 ml of HBS. The number of adhered platelets is determined by protein assay, using the BCA reagent and measuring the absorbance of each well at 562 nM.

Control $A_{562}$ values ranged from 0.3 to 1.0 O.D. and polypeptide I decreased these values by up to 50% in a concentration dependent manner. The $IC_{50}$ for polypeptide I to produce this inhibition is 110 nM.

EXAMPLE 3, 4 and 5

Following the general procedure described in the specification and appropriately modified procedure specifically described in Example 1, polypeptides having Sequence ID Nos. II, III, IV and V were prepared and evaluated for inhibitory activity against platelet adhesion to collagen.

EXAMPLE 6

Sequence ID Nos. I, II, III, IV and V were evaluated for their ability to block platelet adhesion to collagen using the assay described in Example 2 to determine inhibition of platelet adhesion to collagen. An assay similar to the assay described in Example 2, with the exception that plates are coated with fibrinogen rather than collagen, for determining inhibition of platelet binding to fibrinogen. Table 1 shows that these polypeptides inhibit ADP-stimulated platelet aggregation, and that Sequence ID No. 5 is most specific for platelet adhesion to collagen.

TABLE 1

| | Inhibition of Platelet Adhesion to Collagen and Fibrinogen | | | | |
|---|---|---|---|---|---|
| | Percent Inhibition of Adhesion | | | | ADP-Stimulated |
| | Collagen | | Fibrinogen | | Aggregation |
| Protein | $IC_{50}$ | Extent | $IC_{50}$ | Extent | $IC_{50}$ |
| I | .11 | 50 | .27 | 95 | .03 |
| V | .53 | 58 | >8 | 55 @ 10 mM | .80 |
| II | .95 | 52 | >10 | 55 @ 10 mM | .61 |
| III | .55 | 52 | >7.5 | 43 @ 7.5 mM | .30 |
| IV | .68 | | >7.5 | 44 @ 7.5 mM | .33 |

It is contemplated that these polypeptides may also be prepared through genetic engineering techniques. Thus, based upon the amino acid sequences disclosed herein, one may advantageously prepare a synthetic gene corresponding to a disclosed amino acid sequence and introduce that gene into an appropriate host by appropriate cloning vectors. It is therefore understood that the scope of the invention also includes these polypeptides as they may be prepared by genetic engineering techniques.

Polypeptides of the invention may be administered in any situation where inhibition of human or mammalian platelet adhesion to collagen is desired.

Compositions and methods of the invention are useful in surgery on peripheral arteries (arterial grafts, carotid endarterectomy) and in cardiovascular surgery where manipulation of arteries and organs, and/or the interaction of platelets with artificial surfaces, leads to platelet aggregation and consumption. The aggregated platelets may form thrombi and thromboemboli. Polypeptides of the invention may be administered to these surgical patients to prevent the formation of thrombi and thromboemboli by inhibiting adhesion of platelets to collagen and collagen-stimulated platelet aggregation.

Extracorporeal circulation is routinely used for cardiovascular surgery in order to oxygenate blood. Platelets adhere to surfaces of the extracorporeal circuit. Platelets released from artificial surfaces show impaired hemostatic function. Polypeptides of the invention may be administered to prevent adhesion.

Other applications of these polypeptides include prevention of platelet thrombosis, thromboembolism and reacclusion during and after thrombolytic therapy and prevention of platelet thrombosis, thromboembolism and reacclusion after angioplasty of coronary and other arteries and after coronary artery bypass procedures.

The polypeptides for preventing adhesion of platelets to collagen may be administered by any convenient means which will result in its delivery into the blood stream in substantial amount. They may be combined with other platelet aggregation inhibitors or plasminogen activators in order to inhibit platelet aggregation and disturb aggregated platelets. Intravenous administration is presently contemplated as the preferred administration route. They are soluble in water, and may therefore be effectively administered in solution.

The present invention also includes compositions comprising polypeptides of the invention, methods for inducing thrombolysis and preventing reacclusion in a patient which comprise administering these compositions to patients.

In one exemplary application, a suitable amount of the polypeptide is intravenously administered to a heart attack victim undergoing angioplasty. Administration occurs during or several minutes prior to angioplasty, and is in an amount sufficient to inhibit platelet adhesion to collagen, e.g. an amount which achieves a steady state plasma concentration of between about 0.05-20 mM.

( 1 ) GENERAL INFORMATION:

( i i i ) NUMBER OF SEQUENCES: 5

( v i ) CURRENT APPLICATION DATA:
        ( A ) APPLICATION NUMBER: 07/662,225
        ( B ) FILING DATE: February 27, 1991

( 2 ) INFORMATION FOR SEQ ID NO: 1:

( i ) SEQUENCE CHARACTERISTICS:
        ( A ) LENGTH: 49
        ( B ) TYPE: Amino acids
        ( C ) TOPOLOGY: unknown
    ( i i ) MOLECULE TYPE: Other nucleic acid:
        ( A ) DESCRIPTION: Polypeptide
    ( v i ) ORIGINAL SOURCE:
        ( A ) ORGANISM: Echis carinatus viper
    ( v i i ) IMMEDIATE SOURCE: Synthetic
    ( x ) PUBLICATION INFORMATION:
        ( A ) AUTHORS: Gan et al.
        ( B ) TITLE:
        ( C ) JOURNAL: J. Biol. Chem.
        ( D ) VOLUME: 263
        ( E ) ISSUE: -
        ( F ) PAGES: 19827- 19832
        ( G ) DATE: 1988
        ( H ) DOCUMENT NUMBER:
        ( I ) FILING DATE:
        ( J ) PUBLICATION DATE:
        ( K ) RELEVANT RESIDUES IN SEQ ID NO:
    ( x ) PUBLICATION INFORMATION:
        ( A ) AUTHORS: Garsky et al.
        ( B ) TITLE:
        ( C ) JOURNAL: Proc. Natl. Acad. Sci. USA
        ( D ) VOLUME: 86
        ( E ) ISSUE: -
        ( F ) PAGES: 4022- 4026
        ( G ) DATE: 1989
        ( H ) DOCUMENT NUMBER:
        ( I ) FILING DATE:
        ( J ) PUBLICATION DATE:
        ( K ) RELEVANT RESIDUES IN SEQ ID NO:
    ( x ) PUBLICATION INFORMATION:
        ( A ) AUTHORS: Gan et al.
        ( B ) TITLE:
        ( C ) JOURNAL: Gene
        ( D ) VOLUME: 79
        ( E ) ISSUE: -
        ( F ) PAGES: 159- 166
        ( G ) DATE: 1989
        ( H ) DOCUMENT NUMBER:
        ( I ) FILING DATE:
        ( J ) PUBLICATION DATE:
        ( K ) RELEVANT RESIDUES IN SEQ ID NO:
    ( x i ) SEQUENCE DESCRIPTION: SEQ ID NO: 1:

```
Glu  Cys  Glu  Ser  Gly  Pro  Cys  Cys  Arg  Asn  Cys  Lys  Phe  Leu  Lys  Glu
1                  5                       10                      15
Gly  Thr  Ile  Cys  Lys  Arg  Ala  Arg  Gly  Asp  Asp  Met  Asp  Asp  Tyr  Cys
```

```
                    20                    25                        30
Asn Gly Lys Thr Cys Asp Cys Pro Arg Asn Pro His Lys Gly Pro Ala
            35                    40                    45
Thr
49
```

(2) INFORMATION FOR SEQ ID NO: 2:
    (i) SEQUENCE CHARACTERISTICS:
        (A) LENGTH: 49
        (B) TYPE: Amino acids
        (C) TOPOLOGY: unknown
    (ii) MOLECULE TYPE: Other nucleic acid;
        (A) DESCRIPTION: Polypeptide
    (vii) IMMEDIATE SOURCE: Synthetic
    (x) PUBLICATION INFORMATION:
        (A) AUTHORS: Garsky et al.
        (B) TITLE:
        (C) JOURNAL: Proc. Natl. Acad. Sci. USA
        (D) VOLUME: 86
        (E) ISSUE: -
        (F) PAGES: 4022-4026
        (G) DATE: 1989
        (H) DOCUMENT NUMBER:
        (I) FILING DATE:
        (J) PUBLICATION DATE:
        (K) RELEVANT RESIDUES IN SEQ ID NO:
    (xi) SEQUENCE DESCRIPTION: SEQ ID NO: 2:

```
Glu Cys Glu Ser Gly Pro Cys Cys Arg Asn Cys Lys Phe Leu Lys Glu
1               5                   10                      15
Gly Thr Ile Cys Lys Arg Ala Ala Gly Asp Asp Met Asp Asp Tyr Cys
            20                  25                      30
Asn Gly Lys Thr Cys Asp Cys Pro Arg Asn Pro His Lys Gly Pro Ala
            35                  40                  45
Thr
49
```

(2) INFORMATION FOR SEQ ID NO: 3:
    (i) SEQUENCE CHARACTERISTICS:
        (A) LENGTH: 49
        (B) TYPE: Amino acids
        (C) TOPOLOGY: unknown
    (ii) MOLECULE TYPE: Other nucleic acid;
        (A) DESCRIPTION: Polypeptide
    (vii) IMMEDIATE SOURCE: Synthetic
    (x) PUBLICATION INFORMATION:
        (A) AUTHORS:
        (B) TITLE:
        (C) JOURNAL:
        (D) VOLUME:
        (E) ISSUE:
        (F) PAGES:
        (G) DATE:
        (H) DOCUMENT NUMBER:
        (I) FILING DATE:
        (J) PUBLICATION DATE:
        (K) RELEVANT RESIDUES IN SEQ ID NO:
    (xi) SEQUENCE DESCRIPTION: SEQ ID NO: 3:

```
Glu Cys Glu Ser Gly Pro Cys Cys Arg Asn Cys Lys Phe Leu Lys Glu
1               5                   10                      15
Gly Thr Ile Cys Lys Arg Ala Arg Tyr Asp Asp Met Asp Asp Tyr Cys
            20                  25                      30
Asn Gly Lys Thr Cys Asp Cys Pro Arg Asn Pro His Lys Gly Pro Ala
            35                  40                  45
Thr
49
```

(2) INFORMATION FOR SEQ ID NO: 4:
    (i) SEQUENCE CHARACTERISTICS:
        (A) LENGTH: 39
        (B) TYPE: Amino acids
        (C) TOPOLOGY: unknown
    (ii) MOLECULE TYPE: Other nucleic acid;
        (A) DESCRIPTION: Polypeptide
    (vii) IMMEDIATE SOURCE: Synthetic
    (x) PUBLICATION INFORMATION:
        (A) AUTHORS:
        (B) TITLE:
        (C) JOURNAL:
        (D) VOLUME:
        (E) ISSUE:

(F) PAGES:
            (G) DATE:
            (H) DOCUMENT NUMBER:
            (I) FILING DATE.
            (J) PUBLICATION DATE:
            (K) RELEVANT RESIDUES IN SEQ ID NO:
    (xi) SEQUENCE DESCRIPTION: SEQ ID NO: 4:

```
Glu Cys Glu Ser Gly Pro Cys Cys Arg Asn Cys Lys Phe Leu Lys Glu
 1               5                  10                      15
Gly Thr Ile Cys Lys Arg Ala Arg Gly Asp Asp Met Asp Asp Tyr Cys
            20                  25                  30
Asn Gly Lys Thr Cys Asp Cys
            35          39
```

(2) INFORMATION FOR SEQ ID NO: 5:
        (i) SEQUENCE CHARACTERISTICS:
            (A) LENGTH: 39
            (B) TYPE: Amino acids
            (C) TOPOLOGY: unknown
        (ii) MOLECULE TYPE: Other nucleic acid;
            (A) DESCRIPTION: Polypeptide
        (vii) IMMEDIATE SOURCE: Synthetic
        (x) PUBLICATION INFORMATION:
            (A) AUTHORS:
            (B) TITLE:
            (C) JOURNAL:
            (D) VOLUME:
            (E) ISSUE:
            (F) PAGES:
            (G) DATE:
            (H) DOCUMENT NUMBER:
            (I) FILING DATE:
            (J) PUBLICATION DATE:
            (K) RELEVANT RESIDUES IN SEQ ID NO:
    (xi) SEQUENCE DESCRIPTION: SEQ ID NO: 5:

```
Glu Cys Glu Ser Gly Pro Cys Cys Arg Asn Cys Lys Phe Leu Lys Glu
 1               5                  10                      15
Gly Thr Ile Cys Lys Arg Ala Arg Gly Asp Asp Met Asp Asp Tyr Cys
            20                  25                  30
Asn Gly Lys Thr Cys Asp Cys
            35          39
```

What is claimed is:

1. A method for inhibiting collagen-stimulated platelet activation which comprises blocking platelet adhesion to collagen by contacting a polypeptide having the following sequence:

NH$_2$ (Ch) Ala Ala Gly Asp (Cx) COOH    Seq. ID No. 2

NH$_2$ (Ch) Ala Arg Gly Asp (Cy) Z    Seq. ID No. 5.

wherein
    Ch is

Glu Cys Glu Ser Gly Pro Cys Cys Arg Asn Cys Lys
        Phe Leu Lys Glu Gly Thr Ile Cys Lys Arg or conservative amino acid substitutions thereof;
    Cx is Asp Met Asp Asp Tyr Cys Asn Gly Lys Thr Cys Asp
        Cys Pro Arg Asn Pro His Lys Gly Pro Ala Thr or conservative amino acid substitutions thereof;
    Cy is Asp Met Asp Asp Tyr Cys Asn Gly Lys Thr Cys Asp
        Cys or conservative amino acid substitutions thereof;
    and
    Z is NH$_2$ or COOH;

with platelets, in the presence of collagen.

2. A method for inhibiting collagen-stimulated platelet activation in a mammal which comprises blocking platelet adhesion to collagen by contacting a polypeptide having the following sequence:

NH$_2$ (Ch) Ala Ala Gly Asp (Cx) COOH    Seq. ID No. 2

NH$_2$ (Ch) Ala Arg Gly Asp (Cy) Z    Seq. ID No. 5 wherein
    Ch is

Glu Cys Glu Ser Gly Pro Cys Cys Arg Asn Cys Lys
        Phe Leu Lys Glu Gly Thr Ile Cys Lys Arg or conservative amino acid substitutions thereof;
    Cx is Asp Met Asp Asp Tyr Cys Asn Gly Lys Thr Cys Asp
        Cys Pro Arg Asn Pro His Lys Gly Pro Ala Thr or conservative amino acid substitutions thereof;
    Cy is Asp Met Asp Asp Tyr Cys Asn Gly Lys Thr Cys Asp
        Cys or conservative amino acid substitutions thereof;
    and
    Z is NH$_2$ or COOH;

with platelets.

3. A composition for inhibiting collagen-stimulated platelet activation in a mammal by blocking platelet adhesion to collagen, which comprises a polypeptide having the following sequence;

NH₂ (Ch) Ala Ala Gly Asp (Cx) COOH    Seq. ID No. 2

NH₂ (Ch) Ala Arg Gly Asp (Cy) Z    Seq. ID No. 5 wherein
Ch is

Glu Cys Glu Ser Gly Pro Cys Cys Arg Asn Cys Lys
Phe Leu Lys Glu Gly Thr Ile Cys Lys Arg or conservative amino acid substitutions thereof;
Cx is Asp Met Asp Asp Tyr Cys Asn Gly Lys Thr Cys Asp
Cys Pro Arg Asn Pro His Lys Gly Pro Ala Thr or conservative amino acid substitutions thereof;
Cy is Asp Met Asp Asp Tyr Cys Asn Gly Lys Thr Cys Asp
Cys or conservative amino acid substitutions thereof; and
Z is NH₂ or COOH.

* * * * *